United States Patent
Jensen et al.

(10) Patent No.: US 6,969,729 B2
(45) Date of Patent: Nov. 29, 2005

(54) USE OF ISATIN DERIVATIVES AS ION CHANNEL ACTIVATING AGENTS

(75) Inventors: Bo Skaaning Jensen, København S (DK); Tino Dyhring Jørgensen, Solrød Strand (DK); Philip K. Ahring, Bagsværd (DK); Palle Christophersen, Ballerup (DK); Dorte Strøbaek, Farum (DK); Lene Teuber, Værløse (DK); Søren Peter Olesen, Klampenborg (DK)

(73) Assignee: Neurosearch A/S, Ballerup (DK)

( * ) Notice: Subject to any disclaimer, the term of this patent is extended or adjusted under 35 U.S.C. 154(b) by 152 days.

(21) Appl. No.: 10/270,536

(22) Filed: Oct. 16, 2002

(65) Prior Publication Data
US 2003/0114513 A1 Jun. 19, 2003

Related U.S. Application Data

(63) Continuation of application No. 09/854,355, filed on May 15, 2001, now abandoned, which is a continuation of application No. PCT/DK99/00679, filed on Dec. 3, 1999.

(30) Foreign Application Priority Data
Dec. 4, 1998 (DK) ........................................ 1998 01608

(51) Int. Cl.$^7$ ..................... A61K 31/404; C07D 209/04
(52) U.S. Cl. ..................... 514/418; 548/469; 548/483; 544/336; 544/373; 546/201; 514/415
(58) Field of Search ................. 548/469, 483, 548/484, 486; 514/415, 418; 544/336, 373; 546/201

(56) References Cited

U.S. PATENT DOCUMENTS

| | | | |
|---|---|---|---|
| 4,322,533 A | * | 3/1982 | Lesher et al. ............. 546/277.7 |
| 4,780,477 A | | 10/1988 | Kobayashi et al. |
| 5,051,417 A | * | 9/1991 | Nadler et al. ............. 514/222.5 |
| 5,192,792 A | | 3/1993 | Johnson |
| 5,312,928 A | | 5/1994 | Goldin et al. |
| 5,565,483 A | | 10/1996 | Hewawasam et al. |
| 5,602,169 A | | 2/1997 | Hewawasam et al. |
| 5,952,511 A | * | 9/1999 | Esaki et al. .................. 548/486 |
| 6,114,536 A | * | 9/2000 | Esaki et al. ............. 546/277.7 |
| 6,797,692 B1 | * | 9/2004 | Ikonomidou .................... 514/2 |

FOREIGN PATENT DOCUMENTS

| | | |
|---|---|---|
| EP | 010 398 A1 | 4/1980 |
| EP | 432 648 A2 | 6/1991 |

OTHER PUBLICATIONS

Garalene, Lab. Membrane Biophys. vol. 62, No. 3, pp. 20–24, (1999).
Buscarons et al. (1967) : Inform. Quim. Anal. (Madrid), 21 (6), 191–201. STN International Caplus database, Columbus, Ohio, No. 69:27160, 1968.

* cited by examiner

*Primary Examiner*—Golam M. M. Shameem
(74) *Attorney, Agent, or Firm*—Birch, Stewart, Kolasch & Birch, LLP

(57) ABSTRACT

The present invention relates to ion channel activating agents. More particularly, the present invention relates to a particular class of chemical compounds that has proven useful as openers of SKCa and IKCa channels. In further aspects, the present invention relates to the use of these SK/IK channel activating agents for the manufacture of medicaments and pharmaceutical compositions comprising the SK/IK channel activating agents. The SK/IK channel activating agents of the invention are useful for the treatment or alleviation of diseases and conditions associated with the SK/IK channels, in particular respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhea, ischaemia, cerebral ischaemia, ischaemic heart disease, angina pectoris, coronary heart disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labor, baldness, cancer, and immune suppression.

8 Claims, No Drawings

USE OF ISATIN DERIVATIVES AS ION CHANNEL ACTIVATING AGENTS

This application is a continuation of application Ser. No. 09/854,355, filed on May 15, 2001, now abandoned which is a continuation of PCT/DK99/00679 filed Dec. 3, 1999, the entire contents of which are hereby incorporated by reference and for which priority is claimed under 35 U.S.C. §120; and this application claims priority of Application No. 199801608 filed in DENMARK on Dec. 4, 1998 under 35 U.S.C. §119.

TECHNICAL FIELD

The present invention relates to ion channel activating agents. More particularly, the present invention relates to a particular class of chemical compounds that has proven useful as openers of $SK_{Ca}$ and $IK_{Ca}$ channels. In further aspects, the present invention relates to the use of these SK/IK channel activating agents for the manufacture of medicaments, and pharmaceutical compositions comprising the SK/IK channel activating agents.

The SK/IK channel activating agents of the invention are useful for the treatment or alleviation of diseases and conditions associated with the SK/IK channels, in particular respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

Many drugs exert their effects via modulation of ion channels. Examples are anti-epileptic compounds like Phenytoin and Lamotrigine, which block voltage dependent $Na^+$-channels in the brain, anti-hypertensive drugs like Nifedipine and Diltiazem, which block voltage dependent $Ca^{2+}$-channels in smooth muscle cells, and stimulators of insulin release like Glibenclamide and Tolbutamide, which block an ATP-regulated $K^+$-channel in the pancreas.

All mammalian cells express potassium ($K^+$) channels in their cell membranes, and the channels play a dominant role in the regulation of the membrane potential. In nerve and muscle cells they regulate the frequency and form of the action potential, the release of neurotransmitters, and the degree of broncho- and vasodilation.

From a molecular point of view, the $K^+$ channels represent the largest and most diverse group of ion channels. For an overview they can be divided into five large subfamilies: Voltage-activated $K^+$ channels ($K_v$), long QT related $K^+$ channels (KvLQT), inward rectifiers ($K_{IR}$), two-pore $K^+$ channels ($K_{TP}$), and calcium-activated $K^+$ channels ($K_{ca}$).

The latter group, the $Ca^{2+}$-activated $K^+$ channels, consists of three well-defined defined subtypes: SK channels, IK channels and BK channels. SK, IK and BK refer to the single-channel conductance (Small, Intermediate and Big conductance K channel). The SK, IK, and BK channels exhibit differences in e.g. voltage- and calcium-sensitivity, pharmacology, distribution and function.

$Ca^{2+}$-activated SK channels are present in many central neurons and ganglia, where their primary function is to hyperpolarize nerve cells following one or several action potentials to prevent long trains of epileptogenic activity to occur. The SK channels are also present in several peripheral cells including skeletal muscle, gland cells, liver cells, and T-lymphocytes.

The significance of SK channels in normal skeletal muscle is not clear, but their number is significantly increased in denervated muscle, and the large number of SK channels in the muscle of patients with myotonic muscle dystrophia suggest a role in the pathogenesis of the disease.

A number of blockers of SK channels exist, e.g. apamin, atracurium, pancuronium, and tubocurarine, and they are all positively charged molecules which act as pore blockers.

The $Ca^{2+}$-activated IK channel shares a number of characteristics with the $Ca^{2+}$-activated SK channel, since it is highly K-selective, is activated by sub-micromolar concentrations of $Ca^{2+}$, and has an inwardly rectifying conductance. However, there are also striking differences. The unit conductance of the IK channel is 4–5 fold higher than that of the SK channel, and the distribution of the IK channel is restricted to the blood and vasculature. Thus, the IK channel is not expressed in the nervous system and in muscle, but in endothelial cells, cells of epithelial origin and in red blood cells.

In the red blood cells, where the IK channel has been denominated the Gardos channel, a rise in the concentration of intracellular $Ca^{2+}$ opens the channel and causes potassium loss and cell dehydration, a condition which is exacerbated in sickle cell anemia. Promising therapeutic approaches for sickle cell anemia involve specific block of the IK channel.

IK channels have also been implicated in the microvasculature of the kidney, where they may be responsible for the vasodilatory effects of bradykinin. The decrease in blood pressure during septic shock is caused by an increased NO production by the endothelial cells, and the IK channels in these cells are responsible for maintaining the $Ca^{2+}$ influx activating the $Ca^{2+}$-sensitive NO-synthase.

In brain capillary endothelial cells, IK channels, activated by endothelin that is produced by neurons and glia, shunt excess $K^+$ into the blood. Neurotrophilic granulocytes, i.e. mobile phagocytic cells that defend the body against microbial invaders, undergo large depolarisation subsequent to agonistic stimulation, and IK channels have been implicated in depolarising the stimulated granulocyte.

EP 432,648 describes isatin derivatives having excitatory amino acid antagonising activity. However, EP 432,648 does not teach or suggest any SK or IK channel activity associated with these isatin compounds.

SUMMARY OF THE INVENTION

According to the present invention it has now been found that a particular group of isatin derivatives possess valuable activity as openers of $SK_{Ca}$ and/or $IK_{Ca}$ channels, and the invention is directed to isatin derivatives for use as SK/IK channel activating agents.

In its first aspect the invention relates to the use of a isatin derivative represented by the general formula

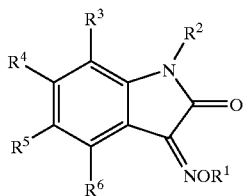

(I)

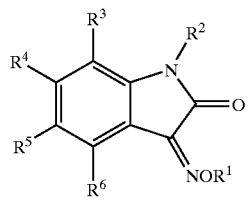

(I)

or a pharmaceutically acceptable salt or an oxide or a hydrate thereof,
wherein, $R^1$ represents hydrogen; an alkyl group; a cycloalkyl group; an acyl group; a phenyl or a benzyl group, which phenyl and benzyl groups may be substituted one or more times with substituents selected from halogen, $-NO_2$, $-CN$, $-CF_3$, alkyl, cycloalkyl, hydroxy, and alkoxy; a group of the formula $-CH_2CN$; a group of the formula $-CH_2CO_2R'$, wherein R' represents hydrogen or alkyl; a group of the formula $-CH_2CONR^{IV}R^V$, wherein $R^{IV}$ and $R^V$ independently represents hydrogen, alkyl, phenyl or benzyl, which phenyl and benzyl groups may optionally be substituted one or more times with halogen and/or alkyl, or $R^{IV}$ and $R^V$ together with the N-atom to which they are attached form a heterocyclic 4 to 7 membered monocyclic group, which heterocyclic group may optionally be substituted one or more times with substituents selected from the group consisting of halogen, alkyl, cycloalkyl, alkyloxy, cycloalkyloxy, phenyl or benzyl; or a group of the formula $-CH_2C(=NOH)NH_2$;

$R^2$ represents hydrogen; an alkyl group; a cycloalkyl group; a group of the formula $-CH_2CO_2R'$, wherein R' represents hydrogen or an alkyl group; a phenyl or a benzyl group, which phenyl and benzyl groups may be substituted one or more times with substituents selected from halogen, $-NO_2$, $-CN$, $-CF_3$, alkyl, cycloalkyl, hydroxy, and alkoxy; and $R^3$, $R^4$, $R^5$, and $R^6$ independently of each another represents hydrogen; halogen; $-NO_2$; $-CN$; $-CF_3$; an alkyl group; an alkoxy group; a phenyl or a benzyl group, which phenyl and benzyl groups may be substituted one or more times with substituents selected from halogen, $-NO_2$, $-CN$, $-CF_3$, alkyl, cycloalkyl, hydroxy, and alkoxy; or a group of the formula $-SO_2NR"R'''$, wherein R" and R''' independently of each another represents hydrogen or an alkyl group;

or $R^5$ and $R^6$ are as defined above, and $R^3$ and $R^4$ together form an additional 4 to 7 membered fused ring, which fused ring may be aromatic, saturated or partially saturated, and which fused ring may optionally be substituted one or more times with substituents selected from the group consisting of halogen, $-NO_2$, $-CN$, $-CF_3$, and a group of the formula $-SO_2NR"R'''$, wherein R" and R''' independently of each another represents hydrogen or an alkyl group;

for the manufacture of a medicament for the treatment or alleviation of a disease or disorder or condition that is responsive to activation of $SK_{Ca}$ and/or $IK_{Ca}$ channels.

In a second aspect, the invention provides novel isatin derivatives having the general formula or a pharmaceutically acceptable salt or an oxide or a hydrate thereof,
wherein, $R^1$ represents hydrogen; a $C_{1-6}$-alkyl group; a group of the formula $-CH_2CO_2R'$, wherein R' represents hydrogen or $C_{1-3}$-alkyl; a group of the formula $-CH_2NH-Z$, wherein Z represents phenyl or benzyl, which phenyl and benzyl may optionally be substituted one or more times with halogen; or a group of the formula $-CH_2CO-Y$, wherein Y represents a heterocyclic 6 membered monocyclic group containing at least one nitrogen atom as the heteroatom, and which heterocyclic group may optionally be substituted one or more times with a $C_{1-6}$-alkyl group or a phenyl group.

$R^2$ represents hydrogen; a $C_{1-6}$-alkyl group; a group of the formula $-CH_2CO_2R'$, wherein R' represents hydrogen or an alkyl group; and $R^3$, $R^4$, $R^5$, and $R^6$ independently of each another represents hydrogen, halogen or a $C_{1-3}$-alkyl group;

or $R^5$ and $R^6$ are as defined above, and $R^3$ and $R^4$ together form an additional 6 membered aromatic or heteroaromatic fused ring.

In a third aspect the invention provides pharmaceutical compositions comprising a therapeutically-effective amount of the isatin derivative of the invention, or a pharmaceutically-acceptable addition salt thereof, together with at least one pharmaceutically-acceptable carrier or diluent.

In a fourth aspect, the invention provides a method for the treatment or alleviation of a disease or disorder or condition of a living animal body, including a human, which disorder or disease or condition is responsive to activation of $SK_{Ca}$ and/or $IK_{Ca}$ channels, comprising the step of administering to such a living animal body, including a human, in need thereof a therapeutically effective amount of a compound of the invention.

The compounds of the invention are particularly useful for the treatment or alleviation of asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immunesuppression.

DETAILED DISCLOSURE OF THE INVENTION

According to the present invention it has now been found that a particular group of isatin derivatives possess valuable activity as openers of $SK_{Ca}$ and/or $IK_{Ca}$ channels.

SK/IK Activating Agents

In the context of this invention, chemical compounds capable of opening $SK_{Ca}$ and/or $IK_{Ca}$ channels are designated SK/IK channel activating agents. The SK/IK channel activating agents of the invention belongs to a particular class of isatin derivatives (alternatively designated indole-2,3-dione-3-oxime derivatives), represented by the following general formula

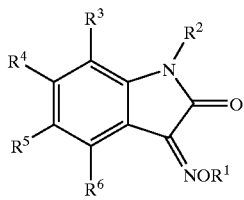

(I)

or a pharmaceutically acceptable salt or an oxide or a hydrate thereof, wherein, $R^1$ represents hydrogen; an alkyl group; a cycloalkyl group; an acyl group; a phenyl or a benzyl group, which phenyl and benzyl groups may be substituted one or more times with substituents selected from halogen, —$NO_2$, —CN, —$CF_3$, alkyl, cycloalkyl, hydroxy, and alkoxy; a group of the formula —$CH_2CN$; a group of the formula —$CH_2CO_2R'$, wherein R' represents hydrogen or alkyl; a group of the formula —$CH_2CONR^{IV}R^V$, wherein $R^{IV}$ and $R^V$ independently represents hydrogen, alkyl, phenyl or benzyl, which phenyl and benzyl groups may optionally be substituted one or more times with halogen and/or alkyl, or $R^{IV}$ and $R^V$ together with the N-atom to which they are attached form a heterocyclic 4 to 7 membered monocyclic group, which heterocyclic group may optionally be substituted one or more times with substituents selected from the group consisting of halogen, alkyl, cycloalkyl, alkyloxy, cycloalkyloxy, phenyl or benzyl; or a group of the formula —$CH_2C(=NOH)NH_2$;

$R^2$ represents hydrogen; an alkyl group; a cycloalkyl group; a group of the formula —$CH_2CO_2R'$, wherein R' represents hydrogen or an alkyl group; a phenyl or a benzyl group, which phenyl and benzyl groups may be substituted one or more times with substituents selected from halogen, —$NO_2$, —CN, —$CF_3$, alkyl, cycloalkyl, hydroxy, and alkoxy; and $R^3$, $R^4$, $R^5$, and $R^6$ independently of each another represents hydrogen; halogen; —$NO_2$; —CN; —$CF_3$; an alkyl group; an alkoxy group; a phenyl or a benzyl group, which phenyl and benzyl groups may be substituted one or more times with substituents selected from halogen, —$NO_2$, —CN, —$CF_3$, alkyl, cycloalkyl, hydroxy, and alkoxy; or a group of the formula —$SO_2NR"R'''$, wherein R' and R" independently of each another represents hydrogen or an alkyl group;

or $R^5$ and $R^6$ are as defined above, and $R^3$ and $R^4$ together form an additional 4 to 7 membered fused ring, which fused ring may be aromatic, saturated or partially saturated, and which fused ring may optionally be substituted one or more times with substituents selected from the group consisting of halogen, —$NO_2$, —CN, —$CF_3$, and a group of the formula —$SO_2NR"R'''$, wherein R" and R''' independently of each another represents hydrogen or an alkyl group;

for the manufacture of a medicament for the treatment or alleviation of a disease or disorder or condition that is responsive to activation of $SK_{Ca}$ and/or $IK_{Ca}$ channels.

In a preferred embodiment, $R^1$ of formula I represents hydrogen; a $C_{1-6}$-alkyl group; a phenyl group; a benzyl group; a group of the formula —$CH_2CO_2R'$, wherein R' represents hydrogen or a $C_{1-6}$-alkyl group; a group of the formula —$CH_2NH$—Z, wherein Z represents phenyl or benzyl, which phenyl and benzyl may optionally be substituted one or more times with halogen; or a group of the formula —$CH_2CO$—Y, wherein Y represents a heterocyclic 6 membered monocyclic group containing at least one nitrogen atom as the heteroatom, and which heterocyclic group may optionally be substituted one or more times with a $C_{1-6}$-alkyl group or a phenyl group. Y preferably represents a piperidinyl or a piperazinyl group.

In another embodiment, $R^2$ of formula I represents hydrogen, $C_{1-6}$-alkyl, phenyl, benzyl, or a group of the formula —$CH_2COOH$.

In a third embodiment, $R^3$, $R^4$, $R^5$, and $R^6$ of formula I independently of each another represents hydrogen, F, Br, Cl, $NO_2$, CN, $CF_3$, or $C_{1-6}$alkyl.

In a fifth embodiment, the isatin derivative for use according to the invention is represented by the general formula

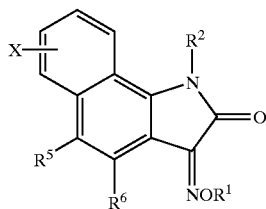

(II)

or a pharmaceutically acceptable salt or an oxide or a hydrate thereof, wherein, $R^1$, $R^2$, $R^5$ and $R^6$ are as defined above; and X represents a substituent selected from the group consisting of hydrogen, halogen, —$NO_2$, —CN, —$CF_3$, and a group of the formula —$SO_2NR"R'''$, wherein R" and R''' independently of each another represents hydrogen or an alkyl group.

In a most preferred embodiment, the isatin derivative for use according to the invention is 5,7-dinitro-1-methyl-1H-indole-2,3-dione-3-(O-methyloxime);
5-bromo-7-nitro-1H-indole-2,3-dione-3-oxime;
5,7-dinitro-1-methyl-1H-indole-2,3-dione-3-oxime;
5-nitro-1H-benziglindole-2,3-dione-3-oxime;
5-nitro-1H-6,7,8,9-tetrahydro-benziglindole-2,3-dione-3-oxime;
5,7-dinitro-1-methyl-1H-indole-2,3-dione-3-(O-methyloxime);
5,7-dinitro-1H-indole-2,3-dione-3-(O-methyloxime);
5,7-dinitro-1-ethyl-1H-indole-2,3-dione-3-(O-methyloxime);
5-nitro-3-(O-methyloxime)-1H-indole-2,3-dione;
1-phenyl-1H-indole-2,3-dione-3-(O-methyloxime);
1H-indole-2,3-dione-3-(O-methyloxime);
5,7-dibromo-1-methyl-1H-indole-2,3-dione-3-(O-methyloxime);
5,7-dibromo-1H-indole-2,3-dione-3-(O-methyloxime);
1-methyl-5-nitro-1H-indole-2,3-dione-3-(O-methyloxime);
5,6-dichloro-1-methyl-1H-indole-2,3-dione-3-(O-methyloxime);
4,5-dichloro-1-methyl-1H-indole-2,3-dione-3-(O-methyloxime);
5,7-dinitro-1-benzyl-1H-indole-2,3-dione-3-(O-methyloxime);

4,6-ditrifluoromethyl-1-methyl-1H-indole-2,3-dione-3-(O-methyloxime);
5-nitro-7-trifluoromethyl-1-methyl-1H-indole-2,3-dione-3-(O-methyloxime);
5-nitro-7-trifluoromethyl-1H-indole-2,3-dione-3-(O-methyloxime);
5,7-dinitro-6-methoxy-1-methyl-1H-indole-2,3-dione-3-(O-methyloxime);
5,7-dinitro-1-(O-ethylcarboxymethyl)-1H-indole-2,3-dione-3-(O-methyloxime);
5-nitro-1-methyl-1H-benziglindole-2,3-dione-3-(O-methyloxime);
5-bromo-1-ethoxycarbonylmethyl)-1H-indole-2,3-dione-3-(O-methyloxime);
5,7-dibromo-1-(ethoxycarbonylmethyl)-1H-indole-2,3-dione-3-(O-methyloxime);
5-methyl-1-(methoxycarbonylmethyl)-1H-indole-2,3-dione-3-(O-ethyloxime);
5-nitro-1-methyl-1H-6,7,8,9-tetrahydro-benz[g]-indole-2,3-dione-3-(O-methyloxime);
1H-benz[g]indole-2,3-dione-3-oxime;
5,7-dinitro-1-methyl-1H-indole-2,3-dione-3-oxime;
5,7-dibromo-1H-indole-2,3-dione-3-oxime;
5-bromo-1-methyl-1H-indole-2,3-dione-3-oxime;
5,7-dinitro-1H-indole-2,3-dione-3-oxime;
5-bromo-7-nitro-1H-indole-2,3-dione-3-oxime;
5-bromo-1H-indole-2,3-dione-3-oxime;
5-nitro-1H-indole-2,3-dione-3-oxime;
5-methyl-1H-indole-2,3-dione-3-oxime;
1H-indole-2,3-dione-3-oxime;
1-methyl-6,7,8,9-tetrahydro-1H-benz[g]indole-2,3-dione-3-oxime;
5,6-dichloro-1-methyl-1H-indole-2,3-dione-3-oxime;
4-phenyl-7-methoxy-1H-indole-2,3-dione-3-oxime;
4,5-dichloro-1H-indole-2,3-dione-3-oxime;
1-phenyl-1H-indole-2,3-dione-3-oxime;
4,5-dichloro-1-methyl-1H-indole-2,3-dione-3-oxime;
5-nitro-1H-benziglindole-2,3-dione-3-oxime;
5-nitro-7-trifluoromethyl-1-methyl-1H-indole-2,3-dione-3-oxime;
5-nitro-7-trifluoromethyl-1H-indole-2,3-dione-3-oxime;
5nitro-1H-6,7,8,9-tetrahydro-benz[g]indole-2,3-dione-3-oxime;
5-fluoro-7-nitro-1H-indole-2,3-dione-3-oxime;
5,7-dinitro-1-(ethoxycarbonylmethyl)-1H-indole-2,3-dione-3-oxime;
1-(ethoxycarbonylmethyl)-1H-indole-2,3-dione-3-oxime;
5-bromo-1-(ethoxycarbonylmethyl)-1H-indole-2,3-dione-3-oxime;
5,7-dinitro-1H-indole-2,3-dione-3-oxime;
5,7-dinitro-1H-indole-2,3-dione-3-(O-benzyloxime);
5,7-dinitro-1H-1-benzyl-indole-2,3-dione-3-(O-benzyloxime);
5,7-dinitro-1-methyl-1H-indole-2,3-dione-3-(O-benzyloxime);
5,7-dinitro-1-(ethoxycarbonylmethyl)-1H-indole-2,3-dione-3-(O-enzyloxime);
5-nitro-1-(ethoxycarbonylmethyl)-1H-indole-2,3-dione-3-(O-benzyloxime);
1-methoxy-1H-indole-2,3-dione-3-oxime;
1-acetyl-5-bromo-1H-indole-2,3-dione;
1-hydroxy-1-H-indole-2,3-dione-3-oxime;
5-bromoisatin 3-oxime;
5,6-dichloro-1-methylisatin 3-oxime;
4,5-dichloroisatin 3-oxime;
4,5-dichloro-1-methylisatin 3-oxime;
O-methyl4,5-dichloro-1-methylisatin 3-oxime;
benz[e]isatin 3-oxime;
6,7-dichloroisatin 3-oxime;
O-methyl 6,7-dichloroisatin 3-oxime;
O-methyl 6,7-dichloro-1-methylisatin 3-oxime;
6,7-dichloro-1-methylisatin 3-oxime;
potassium 2-(6,7-dichloroisatin-1-yl 3-oxime)acetate;
O-t-butyl 6,7-dichloroisatin 3-oxime;
O-((4-phenylpiperazin-1-yl)carbonylmethyl) 6,7-dichloroisatin 3-oxime;
O-(4-chlorobenzylamino)methyl 6,7-dichloroisatin 3-oxime;
6,7-difluoroisatin 3-oxime;
6,7-dimethylisatin 3-oxime;
5,6-dichloroisatin 3-oxime;
O-carboxymethyl 5-bromoisatin 3-oxime;
O-(ethoxycarbonylmethyl) 5-bromoisatin 3-oxime;
O-(carboxymethyl) 6,7-dichloroisatin 3-oxime;
6-chloro-7-methylisatin 3-oxime;
6-fluoro-7-methylisatin 3-oxime; or
6-fluoro-7-methoxyisatin 3-oxime;

or a pharmaceutically acceptable salt or an oxide or a hydrate thereof.

Chemical compounds of formula (I) have been described and may be prepared by methods known in the art, e.g. as disclosed in EP 432,648.

Novel Isatin Derivatives

In another aspect the invention provides novel isatin derivatives represented by the general formula

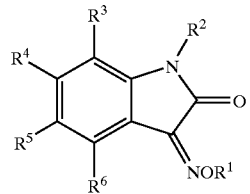

(I)

or a pharmaceutically acceptable salt or an oxide or a hydrate thereof, wherein, $R^1$ represents hydrogen; a $C_{1-6}$-alkyl group; a group of the formula —$CH_2CO_2R'$, wherein R' represents hydrogen or $C_{1-3}$-alkyl; a group of the formula —$CH_2NH$—Z, wherein Z represents phenyl or benzyl, which phenyl and benzyl may optionally be substituted one or more times with halogen; or a group of the formula —$CH_2CO$—Y; wherein Y represents a heterocyclic 6 membered monocyclic group containing at least one nitrogen atom as the heteroatom, and which heterocyclic group may optionally be substituted one or more times with a $C_{1-6}$-alkyl group or a phenyl group;

$R^2$ represents hydrogen; a $C_{1-6}$-alkyl group; a group of the formula —$CH_2CO_2R'$, wherein R' represents hydrogen or an alkyl group; and $R^3$, $R^4$, $R^5$, and $R^6$ independently of each another represents hydrogen, halogen or a $C_{1-3}$-alkyl group;

or $R^5$ and $R^6$ are as defined above, and $R^3$ and $R^4$ together form an additional 6 membered aromatic or heteroaromatic fused ring.

In a most preferred embodiment, the novel isatin derivative of the invention is 5-bromoisatin 3-oxime;
5,6-dichloro-1-methylisatin 3-oxime;
4,5-dichloroisatin 3-oxime;
4,5-dichloro-1-methylisatin 3-oxime;

O-methyl 4,5-dichloro-1-methylisatin 3-oxime;
benz[e]isatin 3-oxime;
6,7-dichloroisatin 3-oxime;
O-methyl 6,7-dichloroisatin 3-oxime;
O-methyl 6,7-dichloro-1-methylisatin 3-oxime;
6,7-dichloro-1-methylisatin 3-oxime;
potassium 2-(6,7-dichloroisatin-1-yl 3-oxime)acetate;
O-t-butyl 6,7-dichloroisatin 3-oxime;
O-((4-phenylpiperazin-1-yl)carbonylmethyl) 6,7-dichloroisatin 3-oxime;
O-(4-chlorobenzylamino)methyl 6,7-dichloroisatin 3-oxime;
6,7-difluoroisatin 3-oxime;
6,7-dimethylisatin 3-oxime;
5,6-dichloroisatin 3-oxime;
O-carboxymethyl 5-bromoisatin 3-oxime;
O-(ethoxycarbonylmethyl) 5-bromoisatin 3-oxime;
O-(carboxymethyl) 6,7-dichloroisatin 3-oxime;
6-chloro-7-methylisatin 3-oxime;
6-fluoro-7-methylisatin 3-oxime; or
6-fluoro-7-methoxyisatin 3-oxime;

or a pharmaceutically acceptable salt or an oxide or a hydrate thereof.

The novel isatin derivatives of the invention may be prepared by the skilled person by conventional methods, using commercially available starting materials. In a preferred embodiment, the isatin derivatives of the invention are prepared using the methods described in the working examples below.

Definition of Substituents

In the context of this invention halogen represents a fluorine, a chlorine, a bromine or a iodine atom.

In the context of this invention an alkyl group designates a univalent saturated, straight or branched hydrocarbon chain. The hydrocarbon chain preferably contain of from one to twelve carbon atoms ($C_{1-12}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a most preferred embodiment alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, and cyclohexyl.

In the context of this invention an alkoxy group designates an "alkyl-O—" group, wherein alkyl is as defined above.

In the context of this invention an acyl group designates a carboxy group or an alkylcarbonyl group, wherein alkyl is as defined above. Examples of preferred acyl groups of the invention are carboxy, acetyl, and propionyl.

In the context of this invention a mono-heterocyclic group is a monocyclic compound, which holds one or more heteroatoms in its ring structure. Preferred heteroatoms include nitrogen (N), oxygen (O), and sulphur (S). One or more of the ring structures may in particular be aromatic (i.e. a heteroaryl or heteroaromatic group), saturated or partially saturated. Preferred heterocyclic monocyclic groups of the invention include 5- and 6 membered heterocyclic monocyclic groups.

Examples of preferred saturated or partially saturated heterocyclic monocyclic groups of the invention include 1,3,5,6,2-dioxadiazinyl, 1,2,3,4,5-, 1,2,3,5,4-dioxadiazolyl, dioxanyl, 1,3-dioxolyl, 1,3,5,6,2-dithiadiazinyl, 1,2,3,4,5- or 1,2,3,5,4-dithiadiazolyl, 2-isoimidazolyl, isopyrrolyl, isotetrazolyl, 1,2,3- or 1,2,4-isotriazolyl, morpholinyl, oxadiazinyl, 1,2,4-, 1,2,6-, 1,3,2-, 1,3,6- or 1,4,2-oxazinyl, piperazinyl, homopiperazinyl, piperidinyl, 1,2-, 1,3- or 1,4-pyranyl, and 1,2,3-pyrrolidinyl. Most preferred heterocyclic 6 membered monocyclic groups of the invention are piperidinyl an piperazinyl.

Examples of preferred aromatic heterocyclic monocyclic groups of the invention include 1,3,2,4- or 1,3,4,5-dioxadiazolyl, dioxatriazinyl, dioxazinyl, 1,2,3-, 1,2,4-, 1,3,2- or 1,3,4-dioxazolyl, 1,3,2,4- or 1,3,4,5-dithiadiazolyl, dithiatriazinyl, dithiazinyl, 1,2,3-dithiazolyl, 2- or 3-furanyl, furazanyl, 1,2 or 4-imidazolyl, isoindazolyl, isothiazol-3,4 or 5-yl, isoxazol-3,4 or 5-yl, 1,2,3-, 1,2,4-, 1,2,5- or 1,3,4-oxadiazol-3,4 or 5-yl, oxatetrazinyl, oxatriazinyl, 1,2,3,4- or 1,2,3,5-oxatriazolyl, oxazol-2,4 or 5-yl, 2 or 3-pyrazinyl, 1,3 or 4-pyrazolyl, 3 or 4-pyridazinyl, 2,3 or 4-pyridinyl, 2,4 or 5-pyrimidinyl, 1,2 or 3-pyrrolyl (azolyl), 1,2,3,4- or 2,1,3,4-tetrazolyl, thiadiazol-3,4 or 5-yl, thiazol-2,4 or 5-yl, 2 or 3-thienyl, 1,2,3-, 1,2,4- or 1,3,5-triazinyl, and 1,2,3-, 1,2,4-, 2,1,3- or 4,1,2-triazolyl. Most preferred heterocyclic 6 membered monocyclic groups of the invention are 1-, 2- or 3-pyridinyl, 2,4,5 or 6-pyrimidinyl, and 2,3,5 or 6-pyrazinyl.

Pharmaceutically Acceptable Salts

The SK/IK channel activating agents of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

The chemical compound of the invention may be provided in unsolved or solvated forms together with a pharmaceutically acceptable solvents such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolved forms for the purposes of this invention.

Steric Isomers

The SK/AK channel activating agents of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Biological Activity

According to the present invention it has now been found that the isatin derivatives of the invention possess valuable activity as openers of $SK_{Ca}$ and/or $IK_{Ca}$ channels.

The SK/IK channel activating activity may be monitored using conventional electrophysiological methods such as patch-clamp techniques, or conventional spectroscopic methods such as FLIPR assay (Fluorescence Image Plate Reader; available from Molecular Devices). These methods generally comprises subjecting an $SK_{Ca}$ or $IK_{Ca}$ containing cell to the action of the chemical compound of the invention, followed by monitoring the membrane potential of the $SK_{Ca}$ or $IK_{Ca}$ containing cell in order to identify changes in the membrane potential caused by the action of the compound of the invention.

In Example 5 the biological activity of the compounds of the invention is demonstrated using electrophysiologic patch-clamp techniques.

Based on their biological activity the compounds of the invention are considered useful for the treatment or alleviation of diseases or conditions responsive to activation of $SK_{Ca}$ and/or $IK_{Ca}$ channels, including diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary, hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

The compounds of the invention is considered particularly useful for reducing or inhibiting undesired immunoregulatory actions. In a preferred embodiment, therefore, the compounds of the may be used in the treatment or alleviation of a diseases, disorders or condition related to immune dysfunction, or in order to obtain immune suppression in an individual in need herefore.

In another, and still more preferred embodiment, the invention relates to the use of a compound of the invention in a combination therapy with known immune-suppressants for the treatment or alleviation of a diseases, disorders or condition related to immune dysfunction, or for obtaining immune suppression. Preferred immune-suppressants to combine with the compounds of the invention include the calcineurin inhibitors (i.e. protein phosphatase 2B inhibitors), in particular Cyclosporin, and FK506.

Conditions which may benefit from this treatment include, but are not limited to diseases, disorders or conditions such as autoimmune diseases, e.g. Addison's disease, alopecia areata, Ankylosing spondylitis, hemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, autoimmune asthma, autoimmune hemolysis, Bechet's disease, Boeck's disease, inflammatory bowel disease, Burkitt's lymphoma, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune-demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome virus (AIDS or EBV) associated B cell lymphoma, parasitic diseases such as Lesihmania, and immunosuppressed disease states such as viral infections following allograft transplantations, graft vs. Host syndrome, transplant rejection, or AIDS, cancers, chronic active hepatitis diabetes, toxic chock syndrome, food poisoning, and transplant rejection.

Pharmaceutical Compositions

In another aspect the invention provides novel pharmaceutical compositions comprising a therapeutically effective amount of a chemical compound having $SK_{Ca}$ or $IK_{Ca}$ activating activity.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the SK/IK channel activating agents of the invention, or a pharmaceutically acceptable salt or derivative thereof, together with one or more pharmaceutically acceptable carriers therefor, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, and intravenous injection) administration, or those in a form suitable for administration by inhalation or insufflation.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating-material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethyicellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 $\mu$g/kg i.v. and 1 $\mu$g/kg p.o. The upper limit of the dosage range is presently considered to be about 10 mg/kg i.v. and 100 mg/kg p.o. Preferred ranges are from about 0.1 $\mu$g/kg to about 10 mg/kg/day i.v., and from about 1 $\mu$g/kg to about 100 mg/kg/day p.o.

Methods of Theraphy

In another aspect the invention provides a method for the treatment or alleviation of a disease or disorder or condition of a living animal body, including a human, which disorder or disease or condition is responsive to activation of $SK_{Ca}$ and/or $IK_{Ca}$ channels, comprising the step of administering to such a living animal body, including a human, in need thereof a therapeutically effective amount of a compound of the invention.

In a preferred embodiment, the disease or disorder or condition is a respiratory disease such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy,: Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples which are not intended to be in any way limiting to the scope of the invention as claimed.

filtered off. Recrystallisation from ethanol afforded pure 5-bromoisatin 3-oxime (2.2 g, 91%). Mp. 250–251° C.

The following compounds were prepared analogously:

5,6-dichloro-1-methylisatin 3-oxime (1b) from 5,6-dichloro-1-methylisatin. Yield: 79%. Mp. 232–236° C.
4,5-dichloroisatin 3-oxime (1c) from 4,5-dichloroisatin. Yield: 51%. Mp. 245–247° C.

TABLE I

Substituted isatin oximes

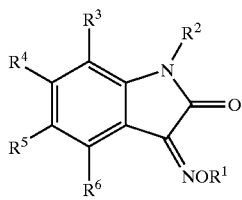

| Entry | $R_1$ | $R_2$ | $R_3$ | $R_4$ | $R_5$ | $R_6$ | Mp. | Examples |
|---|---|---|---|---|---|---|---|---|
| 1a | H | H | H | H | Br | H | 250-1 | 1, 3 |
| 1b | H | $CH_3$ | H | Cl | Cl | H | 232-6 | 1, 2, 3 |
| 1c | H | H | H | H | Cl | Cl | 245-7 | 1, 3 |
| 1d | H | $CH_3$ | H | H | Cl | Cl | 140-2 | 1, 2, 3 |
| 1e | $CH_3$ | $CH_3$ | H | H | Cl | Cl | 180-3 | 1, 2, 3 |
| 1f | H | H | H | H | —CH=CH—CH=CH— | | 230 | 1, 4 |
| 1g | H | H | Cl | Cl | H | H | 277-8 | 1, 3 |
| 1h | $CH_3$ | H | Cl | Cl | H | H | >250 | 1, 3 |
| 1i | $CH_3$ | $CH_3$ | Cl | Cl | H | H | 189-91 | 1, 2, 3 |
| 1j | H | $CH_3$ | Cl | Cl | H | H | >200 | 1, 2, 3 |
| 1k | H | $CH_2$—COOH | Cl | Cl | H | H | >300 | 1, 2a, 3 |
| 1l | t-Bu | H | H | Cl | Cl | H | H | 220-1 | 1, 3 |
| 1m | ![structure] | H | Cl | Cl | H | H | 237-8 | 1, 3 |
| 1n | $CH_2NHCH_2$ Ph(4)Cl | H | Cl | Cl | H | H | 232-4 | 1, 3 |
| 1o | H | H | F | F | H | H | 263-4 | 1, 3 |
| 1p | H | H | $CH_3$ | $CH_3$ | H | H | 283-4 | 1, 3 |
| 1q | H | H | H | Cl | Cl | H | 274-5 | 1, 3 |
| 1r | $CH_2COOH$ | H | H | H | Br | H | 214-6 | 1 |
| 1s | $CH_2CO_2Et$ | H | H | H | Br | H | 167-9 | 1 |
| 1t | $CH_2COOH$ | H | Cl | Cl | H | H | 245-6 | 1, 3 |
| 1u | H | H | $CH_3$ | Cl | H | H | >300 | 1, 3 |
| 1v | H | H | $CH_3$ | F | H | H | 286 (decomp.) | 1, 3 |
| 1w | H | H | O—$CH_3$ | F | H | H | 268–270 | 1, 3 |

Example 1

Preparatory Example

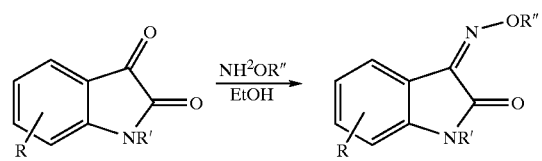

5-Bromoisatin 3-oxime (1a). A mixture of 5-bromoisatin (2.4 g; 10.0 mmol), hydroxylamine, hydrochloride (0.76 g; 11 mmol) and sodium carbonate (1.1 g; 10.4 mmol) in 96% ethanol (30 ml) was stirred at ambient temperature for two hours. Water (50 ml) was added and the crude product was 4,5-dichloro-1-methylisatin 3-oxime (1d) from 4,5-dichloro-1-methylisatin. Yield: 79%. Mp. 140–142° C.
O-methyl-4,5-dichloro-1-methylisatin 3-oxime (1e) from 4,5-dichloro-1-methylisatin and O-methylhydroxylamine, hydrochloride. The reaction mixture was heated to reflux. Yield: 64%. Mp. 180–183° C.
Benzo[e]isatin 3-oxime (1f) from benzo[e]isatin. The reaction mixture was heated to reflux. Mp. 230° C.
6,7-dichloroisatin 3-oxime (1g) from 6,7-dichloroisatin. The reaction mixture was heated to reflux. Yield: 70%. Mp. 277–278° C.
O-methyl 6,7-dichloroisatin 3-oxime (1h) from 6,7-dichloroisatin and O-methyl hydroxylamine, hydrochloride. The reaction mixture was heated to reflux. Yield: 43%. Mp. >250° C.
O-methyl 6,7-dichloro-1-methylisatin 3-oxime (1i) from 6,7-dichloro-1-methylisatin and O-methyl hydroxylamine, hydrochloride. The reaction mixture was heated to reflux. Yield: 74%. Mp. 189–191° C.

6,7-Dichloro-1-methylisatin 3-oxime (1j) from 6,7-dichloro-1-methylisatin. The reaction mixture was heated to reflux. Yield: 52%. Mp. >200° C.

Potassium 2-(6,7-dichloroisatin-1-yl 3-oxime)acetate (1k) from 2-(6,7-dichloroisatin-1-yl)acetic acid (Example 2a). The reaction mixture was heated to reflux. The product precipitated as the potassium salt upon addition of potassium t-butanolate to an ethanolic solution. Yield: 60%. Mp. >300° C.

O-t-butyl 6,7-dichloroisatin 3-oxime (1l) from 6,7-dichloroisatin and O-t-butyl hydroxylamine, hydrochloride. The reaction mixture was heated to reflux. Yield: 78%. Mp. 220–221° C.

O-((4-Phenylpiperazin-1-yl)carbonylmethyl) 6,7-dichloroisatin 3-oxime (1m) from O-((4-phenylpiperazin-1-yl)carbonylmethyl)hydroxylamine, hydrochloride and 6,7-dichloroisatin. The reaction mixture was heated to reflux. Yield: 76%. Mp. 237–238° C.

O-(4-Chlorobenzylamino)methyl 6,7-dichloroisatin 3-oxime (1n) from 6,7-dichloroisatin and O-((4-chlorobenzylamino)methyl) hydroxylamine. The reaction mixture was heated to reflux. Yield: 69%. Mp. 232–234° C.

6,7-Difluoroisatin 3-oxime (1o) from 6,7-difluoroisatin and hydroxylamine, hydrochloride. The reaction mixture was heated to reflux. Yield: 100%. Mp. 263–264° C.

6,7-Dimethylisatin 3-oxime (1p) from 6,7-dimethylisatin and hydroxylamine, hydrochloride. The reaction mixture was heated to reflux. Yield: 98%. Mp. 283–284° C.

5,6-Dichloroisatin 3-oxime (1q) from 5,6-dichloroisatin and hydroxylamine, hydrochloride. The reaction mixture was heated to reflux. Yield: 52%. Mp. 274–275° C.

O-Carboxymethyl 5-bromoisatin 3-oxime (1r) from 5-bromoisatin and O-carboxymethyl hydroxylamine, hydrochloride. THF was used as solvent and the reaction mixture was heated to reflux. Yield: 76%. Mp. 214–216° C.

O-(Ethoxycarbonylmethyl) 5-bromoisatin 3-oxime (1s) from 5-bromoisatin and O-(carboxymethyl)hydroxylamine, hydrochloride. The reaction mixture was heated to reflux and addition of base was omitted. Yield: 6%. Mp. 167–169° C.

O-(Carboxymethyl) 6,7-dichloroisatin 3-oxime (1t) from 6,7-dichloroisatin and O-(carboxymethyl)hydroxylamine, hydrochloride. The reaction mixture was heated to reflux. Yield: 71%. Mp. 245–246° C.

6-Chloro-7-methylisatin 3-oxime (1u) from 6-chloro-7-methylisatin and hydroxylamine, hydrochloride. THF was used as solvent and the reaction mixture was heated to reflux. Yield: 56%. Mp. >300° C.

6-Fluoro-7-methylisatin 3-oxime (1v) from 6-fluoro-7-methylisatin and hydroxylamine, hydrochloride. THF was used as solvent and the reaction mixture was heated to reflux. Yield: 92%. Mp. 286° C. with decomposition.

6-Fluoro-7-methoxyisatin 3-oxime (1w) from 6-fluoro-7-methoxyisatin and hydroxylamine, hydrochloride. THF was used as solvent and the reaction mixture was heated to reflux. Yield: 87%. Mp. 268–270° C.

Example 2

Intermediate Compounds

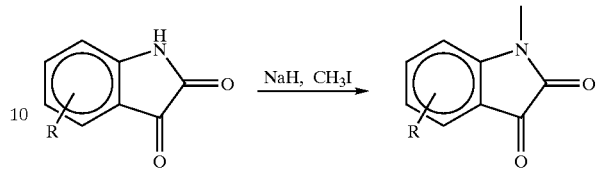

5,6-dichloro-1-methylisatin (2a). To a solution of 5,6-dichloroisatin (0,15 g; 0.7 mmol) in anhydrous DMF (5 ml) was added sodium hydride (40 mg, 60% dispersion in mineral oil). When the evolution of hydrogen had ceased iodomethane (0.1 ml) was added and the mixture was stirred for 20 min. at ambient temperature. Water (15 ml) and glacial acetic acid (0.1 ml) were added and the product was filtered off, washed with water and dried to yield 5,6-dichloro-1-methylisatin (0.13 g, 81%).

The following compounds were prepared analogously:

4,5-dichloro-1-methylisatin (2b) from 4,5-dichloroisatin, and 6,7-dichloro-1-methylisatin from 6,7-dichloroisatin.

Example 2a

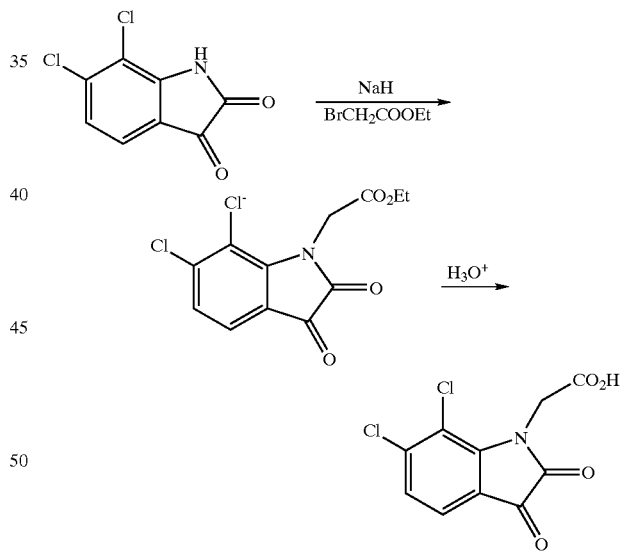

2-(6,7-dichloroisatin-1-yl)acetic acid (2c). A solution of 5,6-dichloroisatin (1.0 g, 4.65 mmol) in DMF (20 ml) was cooled in an ice-bath. Sodium hydride (5.11 mmol, 0.20 g 60% dispersion in mineral oil) was added and the mixture was stirred for 20 min. Ethyl 2-bromoacetate (0.37 ml, 5.11 mmol) was added and stirring was continued for 2 hours. The resulting mixture was poured into diluted hydrochloric acid (200 ml, 4M), heated to reflux for 2 hours, filtered, cooled and extracted with ethyl acetate. The organic extract was dried over magnesium sulphate and evaporated to dryness to leave the desired product (0.85 g, 67%).

Example 3

Intermediate Compounds

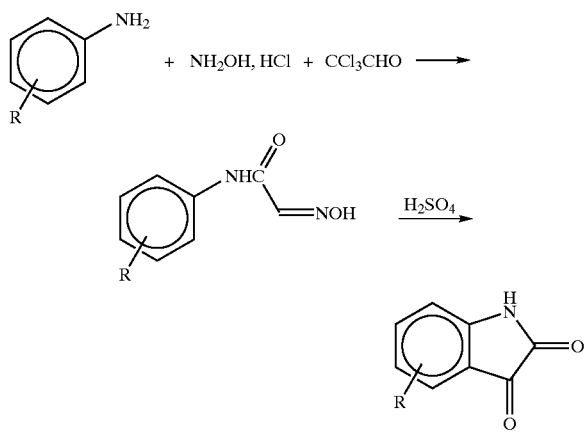

The following isatins were prepared according to the above Scheme, by the procedure described in Organic Syntheses, Coll. Vol. I p. 327.

5,6-dichloroisatin (3a) and 4,dichloroisatin (3b) were prepared as a mixture of isomers from 3,4-dichloroaniline. The isomers were separated by fractionated crystallisation from ethylacetate.

6,7-dichloroisatin (3c) was prepared from 2,3-dichloroaniline.

6,7-difluoroisatin (3d) was prepared from 2,3-difluoroaniline.

6,7-dimethylisatin (3e) was prepared from 2,3-dimethylaniline.

6-chloro-7-methyisatin (3f) was prepared from 3-chloro-2-methylaniline.

6-fluoro-7-methylisatin (3g) was prepared from 3-fluoro-2-methylaniline.

6-fluoro-7-methoxyisatin (3h) was prepared from 3-fluoro-o-anisidine.

Example 4

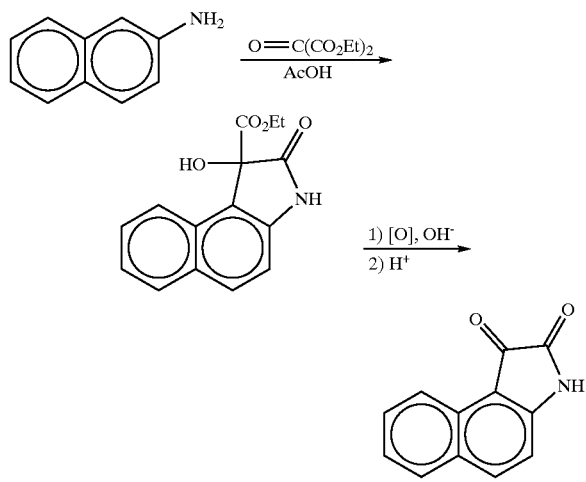

Benzo[e]isatin (4a). A mixture of diethyl oxomalonate (1.4 ml; 9 mmol), 2-aminonaphtalene (1 g; 7 mmol) and sodium carbonate (0.2 g; 1.9 mmol) in acetic acid (15 ml) was heated to reflux for 10 min. The solvent was removed by evaporation and the residue was suspended in aqueous sodium hydroxide (4 M, 30 ml). The suspension was heated to reflux for 5 hours, during which time air was bobbled through the reaction mixture. The cooled mixture was acidified with diluted hydrochloric acid and the crude product was filtered off. Recrystallisation from ethanol afforded pure benzo[e]isatin (0.3 g. Mp. 245° C.).

Example 5

Electrophysiological Experiments

In this example, the biological activity of the compounds of the invention is demonstrated using electrophysiologic patch-clamp techniques.

Intermediate-conductance $Ca^{2+}$-activated $K^+$ channels (IK channels) have been cloned from human placenta and stably expressed in HEK293 cells. The ionic current through the channels is recorded in the whole-cell mode of the patch-clamp technique.

Stable Expression of IK in HEK293 Cells

Human IK (hIK) was excised from pT3T7 (GenBank Acc. No. N56819) using EcoR I and Not I, and subcloned into the mammalian expression vector pNS1Z (NeuroSearch), a custom designed derivative of pcDNA3Zeo (InVitrogen), to give the plasmid construct $pNS1Z_{13}$ hIK.

HEK293 tissue culture cells were grown in DMEM (Dulbecco's Modified Eagle Medium) supplemented with 10% FCS (foetal calf serum) at 37° C. in 5% $CO_2$. One day prior to transfection, $10^6$ cells were plated in a cell culture T25 flask. The following day, cells were transfected using lipofection (20 μL Lipofectamin™, Life Technologies, with 2.5 μg of the plasmid $pNS1Z_{13}$ hIK in a total volume of 540 μL).

The lipofection mixture was overlaid on the cells and incubated at 37° C. for 5 hours. The cells were then rinsed with regular media and grown for 72 hours in DMEM, 10% FCS at 37° C. in 5% $CO_2$.

72 hours post transfection, cells transfected with pNS1Z__ hIK were selected in media supplemented with 0.25 mg/ml Zeocin. Single clones were picked and propagated in selection media until sufficient cells for freezing were available. Hereafter the cells were cultured in regular medium without selection agent.

Expression of functional hIK channels was verified by patch-clamp measurements.

Whole Cell Recordings

Experiments are carried out on one of several patch-clamp set-ups. Cells plated on coverslips are placed in a 15 μl perfusion chamber (flowrate ~1 ml/min) mounted on a IMT-2 microscope equipped with Nomarski or Hoffmann optics. The microscopes are placed on vibration-free tables in grounded Faraday cages. All experiments are performed at room temperature (20–22° C.). EPC-9 patch-clamp amplifiers (HEKA-electronics, Lambrect, Germany) are connected to Macintosh computers via ITC16 interfaces. Data are stored directly on the harddisk and analysed by the IGOR software (WaveMetrics, Lake Oswega, USA).

The whole-cell configuration of the patch clamp technique is applied. The tip of a borosilicate pipette (resistance 2–4 MΩ) is gently (remote control system) placed on the cell membrane. Light suction results in a giga seal (pipette resistance increases to more than 1 GΩ) and the cell membrane is then ruptured by more powerful suction. Cell capacitance is electronically compensated and the resistance between the pipette and the cell interior (the series resistance, Rs) is measured and compensated for. Usually the cell capacitance ranges from 5 to 20 pF (depending on cell size) and the series resistance is in the range 3 to 6 MΩ.

Rs- as well as capacitance compensation are updated during the experiments (before each stimulus).

All experiments with drifting Rs-values are discharged. Leak-subtractions are not performed.

Solutions

The following five compounds, 1a, 1g, 1h, 1i and 1j of Table 1, were subjected to this experiment.

The extracellular (bath) solution contains: 144 mM KCl, 2 mM $CaCl_2$, 1 mM $MgCl_2$, 10 mM HEPES (pH=7.4). Test compounds are dissolved in DMSO from stock solution and then diluted to a final concentration of about 10 µM in the extracellular solution. The concentration of $CaCl_2$ is 7.6 mM and that of $MgCl_2$ is 1.2 mM to give calculated free concentrations of 300 nM and 1 mM, respectively.

Quantification

After establishment of the whole-cell configuration, voltage-ramps (usually −100 to +100 mV) are applied to the cell every 5 sec. A stable baseline current is obtained within a period of 100–300 seconds, and the compounds are then added by changing to an extracellular solution containing the compound to be tested. Very little endogen current (<200 pA at 100 mV, compared to 2–20 nA IK current) are activated under these circumstances in native HEK293 cells.

Results

All compounds tested in this experiment showed activity at a final concentration of about 10 µM or less, and these compounds therefore are potent SK/IK channel activating agents of the invention.

What is claimed is:

1. A method of treatment or alleviation of a disease or disorder or condition of a living animal body, which disorder or disease or condition is at least one selected from the group consisting of asthma, cystic fibrosis, chronic obstructive pulmonary disease, rhinorrhea, urinary incontinence and psychosis, comprising the step of administering to such a living animal body in need thereof a therapeutically effective amount of an isatin compound represented by formula (I)

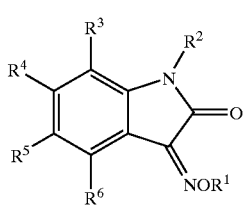

(I)

or a pharmaceutically acceptable salt or an oxide or a hydrate thereof, wherein, $R^1$ represents hydrogen; an alkyl group; a cycloalkyl group; an acyl group; a phenyl or a benzyl group, which phenyl and benzyl groups are unsubstituted or are substituted one or more times with substituents selected from halogen, $—NO_2$, $—CN$, $—CF_3$, alkyl, cycloalkyl, hydroxy, and alkoxy; a group of the formula $—CH_2CN$; a group of the formula $—CH_2CO_2R'$, wherein R' represents hydrogen or alkyl; a group of the formula $—CH_2CONR^{IV}R^V$, wherein $R^{IV}$ and $R^V$ independently represents hydrogen, alkyl, phenyl or benzyl, which phenyl and benzyl groups are unsubstituted or are substituted one or more times with halogen and/or alkyl, or $R^{IV}$ and $R^V$ together with the N-atom to which they are attached form a heterocyclic 4 to 7 membered monocyclic group, which heterocyclic group are unsubstituted or are substituted one or more times with substituents selected from the group consisting of halogen, alkyl, cycloalkyl, alkyloxy, cycloalkyloxy, phenyl or benzyl; or a group of the formula $—CH_2C(=NOH)NH_2$;

$R^2$ represents hydrogen; an alkyl group; a cycloalkyl group; a group of the formula $—CH_2CO_2R'$, wherein R' represents hydrogen or an alkyl group; a phenyl or a benzyl group, which phenyl and benzyl groups are unsubstituted or are substituted one or more times with substituents selected from halogen, $—NO_2$, $—CN$, $—CF_3$, alkyl, cycloalkyl, hydroxy, and alkoxy; and $R^3$, $R^4$, $R^5$, and $R^6$ independently of each another represents hydrogen; halogen; $—NO_2$; $—CN$; $—CF_3$; an alkyl group; an alkoxy group; a phenyl or a benzyl group, which phenyl and benzyl groups are unsubstituted or are substituted one or more times with substituents selected from halogen, $—NO_2$, $—CN$, $—CF_3$, alkyl, cycloalkyl, hydroxy, and alkoxy; or a group of the formula $—SO_2NR''R'''$, wherein R'' and R''' independently of each another represents hydrogen or an alkyl group;

or $R^5$ and $R^6$ are as defined above, and $R^3$ and $R^4$ together form an additional 4 to 7 membered fused ring, which fused ring may be aromatic, saturated or partially saturated, and which fused ring are unsubstituted or are substituted one or more times with substituents selected from the group consisting of halogen, $—NO_2$, $—CN$, $—CF_3$, and a group of the formula $—SO_2NR''R'''$, wherein R'' and R''' independently of each another represents hydrogen or an alkyl group.

2. The method according to claim 1, wherein $R^1$ of formula I represents hydrogen; a $C_{1-6}$-alkyl group; a phenyl group; a benzyl group; a group of the formula $—CH_2CO_2R'$, wherein R' represents hydrogen or a $C_{1-6}$-alkyl group; a group of the formula $—CH_2NH—Z$, wherein Z represents phenyl or benzyl, which phenyl and benzyl are unsubstituted or are substituted one or more times with halogen; or a group of the formula $—CH_2CO—Y$, wherein Y represents a heterocyclic 6 membered monocyclic group containing at least one nitrogen atom as the heteroatom, and which heterocyclic group are unsubstituted or are substituted one or more times with a $C_{1-6}$-alkyl group or a phenyl group.

3. The method according to claim 2, wherein Y represents a piperidinyl or a piperazinyl group.

4. The method according to claim 1, wherein $R^2$ of formula I represents hydrogen, $C_{1-6}$-alkyl, phenyl, benzyl, or a group of the formula $—CH_2COOH$.

5. The method according to any of claims 1–4, wherein $R^3$, $R^4$, $R^5$, and $R^6$ of formula I independently of each another represents hydrogen, F, Br, Cl, $NO_2$, CN, $CF_3$, or $C_{1-6}$-alkyl.

6. The method according to any of claims 1–4, wherein the isatin compound is represented by formula (II)

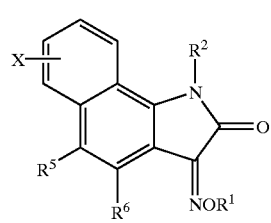

(II)

or a pharmaceutically acceptable salt or an oxide or a hydrate thereof, wherein, R¹, R², R⁵ and R⁶ are as defined above; and X represents a substituent selected from the group consisting of hydrogen, halogen, —NO₂, —CN, —CF₃, and a group of the formula —SO₂NR"R'", wherein R" and R'" independently of each another represents hydrogen or an alkyl group.

7. The method according to claim 1, wherein the isatin compound is 5,7-dinitro-1-methyl-1H-indole-2,3-dione-3-(O-methyloxime);
5-bromo-7-nitro-1H-indole-2,3-dione-3-oxime;
5,7-dinitro-1-methyl-1H-indole-2,3-dione-3-oxime;
5-nitro-1H-benz[g]indole-2,3-dione-3-oxime;
5-nitro-1H-6,7,8,9-tetrahydro-benz[g]indole-2,3-dione-3-oxime;
5,7-dinitro-1-methyl-1H-indole-2,3-dione-3-(O-methyloxime);
5,7-dinitro-1H-indole-2,3-dione-3-(O-methyloxime);
5,7-dinitro-1-ethyl-1H-indole-2,3-dione-3-(O-methyloxime);
5-nitro-3-(O-methyloxime)-1H-indole-2,3-dione;
1-phenyl-1H-indole-2,3-dione-3-(O-methyloxime);
1H-indole-2,3-dione-3-(O-methyloxime);
5,7-dibromo-1-methyl-1H-indole-2,3-dione-3-(O-methyloxime);
5,7-dibromo-1H-indole-2,3-dione-3-(O-methyloxime);
1-methyl-5-nitro-1H-indole-2,3-dione-3-(O-methyloxime);
5,6-dichloro-1-methyl-1H-indole-2,3-dione-3-(O-methyloxime);
4,5-dichloro-1-methyl-1H-indole-2,3-dione-3-(O-methyloxime);
5,7-dinitro-1-benzyl-1H-indole-2,3-dione-3-(O-methyloxime);
4,6-ditrifluoromethyl-1-methyl-1H-indole-2,3-dione-3-(O-methyloxime);
5-nitro-7-trifluoromethyl-1-methyl-1H-indole-2,3-dione-3-(O-methyloxime);
5-nitro-7-trifluoromethyl-1H-indole-2,3-dione-3-(O-methyloxime);
5,7-dinitro-6-methoxy-1-methyl-1H-indole-2,3-dione-3-(O-methyloxime);
5,7-dinitro-1-(O-ethylcarboxymethyl)-1H-indole-2,3-dione-3-(O-methyloxime);
5-nitro-1-methyl-1H-benz[g]indole-2,3-dione-3-(O-methyloxime);
5-bromo-1-ethoxycarbonylmethyl)-1H-indole-2,3-dione-3-(O-methyloxime);
5,7-dibromo-1-(ethoxycarbonyl methyl )-1H-indole-2,3-dione-3-(O-methyloxime);
5-methyl-1-(methoxycarbonylmethyl)-1H-indole-2,3-dione-3-(O-methyloxime);
5-nitro-1-methyl-1H-6,7,8,9-tetrahydro-benz[g]-indole-2,3-dione-3-(O-methyloxime);
1H-benz[g]indole-2,3-dione-3-oxime;
5,7-dinitro-1-methyl-1H-indole-2,3-dione-3-oxime;
5,7-dibromo-1H-indole-2,3-dione-3-oxime;
5-bromo-1-methyl-1H-indole-2,3-dione-3-oxime;
5,7-dinitro-1H-indole-2,3-dione-3-oxime;
5-bromo-7-nitro-1H-indole-2,3-dione-3-oxime;
5-bromo-1H-indole-2,3-dione-3-oxime;
5-nitro-1H-indole-2,3-dione-3-oxime;
5-methyl-1H-indole-2,3-dione-3-oxime;
1H-indole-2,3-dione-3-oxime;
1-methyl-6,7,8,9-tetrahydro-1H-benz[g]indole-2,3-dione-3-oxime;
5,6-dichloro-1-methyl-1H-indole-2,3-dione-3-oxime;
4-phenyl-7-methoxy-1H-indole-2,3-dione-3-oxime;
4,5-dichloro-1H-indole-2,3-dione-3-oxime;
1-phenyl-1H-indole-2,3-dione-3-oxime;
4,5-dichloro-1-methyl-1H-indole-2,3-dione-3-oxime;
5-nitro-1H-benz[g]indole-2,3-dione-3-oxime;
5-nitro-7-trifluoromethyl-1-methyl-1H-indole-2,3-dione-3-oxime;
5-nitro-7-trifluoromethyl-1H-indole-2,3-dione-3-oxime;
5-nitro-1H-6,7,8,9-tetrahydro-benz[g]indole-2,3-dione-3-oxime;
5-fluoro-7-nitro-1H-indole-2,3-dione-3-oxime;
5,7-dinitro-1-(ethoxycarbonylmethyl)-1H-indole-2,3-dione-3-oxime;
1-(ethoxycarbonylmethyl)-1H-indole-2,3-dione-3-oxime;
5-bromo-1-(ethoxycarbonylmethyl)-1H-indole-2,3-dione-3-oxime;
5,7-dinitro-1H-indole-2,3-dione-3-oxime;
5,7-dinitro-1H-indole-2,3-dione-3-(O-benzyloxime);
5,7-dinitro-1H-1-benzyl-indole-2,3-dione-3-(O-benzyloxime);
5,7-dinitro-1-methyl-1H-indole-2,3-dione-3-(O-benzyloxime);
5,7-dinitro-1-(ethoxycarbonylmethyl)-1H-indole-2,3-dione-3-(O-benzyloxime);
5-nitro-1-(ethoxycarbonylmethyl)-1H-indole-2,3-dione-3-(O-benzyloxime);
1-methoxy-1H-indole-2,3-dione-3-oxime;
1-acetyl-5-bromo-1H-indole-2,3-dione;
1-hydroxy-1-H-indole-2,3-dione-3-oxime;
5-bromoisatin 3-oxime;
5,6-dichloro-1-methylisatin 3-oxime;
4,5-dichloroisatin 3-oxime;
4,5-dichloro-1-methylisatin 3-oxime;
O-methyl-4,5-dichloro-1-methylisatin 3-oxime;
benz[e]isatin 3-oxime;
6,7-dichloroisatin 3-oxime;
O-methyl 6,7-dichloroisatin 3-oxime;
O-methyl 6,7-dichloro-1-methylisatin 3-oxime;
6,7-dichloro-1-methylisatin 3-oxime;
potassium 2-(6,7-dichloroisatin-1-yl 3-oxime)acetate;
O-t-butyl 6,7-dichloroisatin 3-oxime;
O-((4-phenylpiperazin-1-yl)carbonylmethyl)6,7 dichloroisatin 3-oxime;
O-(4-chlorobenzylamino)methyl 6,7-dichloroisatin 3-oxime;
6,7-difluoroisatin 3-oxime;
6,7-dimethylisatin 3-oxime;
5,6-dichloroisatin 3-oxime;
O-carboxymethyl 5-bromoisatin 3-oxime;
O-(ethoxycarbonylmethyl) 5-bromoisatin 3-oxime;
O-(carboxymethyl) 6,7-dichloroisatin 3-oxime;
6-chloro-7-methylisatin 3-oxime;
6-fluoro-7-methylisatin 3-oxime; or
6-fluoro-7-methoxyisatin 3-oxime;
or a pharmaceutically acceptable salt or an oxide or a hydrate thereof.

8. The method according to claim 1, wherein said living animal body is a human.

* * * * *